United States Patent [19]

Bernasconi et al.

[11] 4,187,234
[45] Feb. 5, 1980

[54] ALKANECARBOXYLIC ACID COMPOUNDS WHICH HAVE BENZOFURANYL OR BENZOTHIENYL SUBSTITUENTS

[75] Inventors: Raymond Bernasconi, Oberwil; Pier G. Ferrini, Binningen, both of Switzerland

[73] Assignee: Ciba-Geigy Corporation, Ardsley, N.Y.

[21] Appl. No.: 931,055

[22] Filed: Aug. 4, 1978

Related U.S. Application Data

[63] Continuation of Ser. No. 798,272, May 19, 1977, abandoned.

[30] Foreign Application Priority Data

May 31, 1976 [CH] Switzerland .................. 6783/76

[51] Int. Cl.$^2$ ............................................ C07D 307/80
[52] U.S. Cl. ............................ 260/346.22; 260/346.7; 546/269; 546/274; 549/58; 549/52
[58] Field of Search ........... 260/346.22, 330.5, 346.73; 546/269

[56] References Cited
PUBLICATIONS

Goldenberg el al., Chimie Thérapeutique, Jul.–Aug. 1973, No. 4, pp. 398–411.
LaForge, J.A.C.S., vol. 56, Jul. 1933, pp. 3040–3048.

*Primary Examiner*—Alan L. Rotman
*Assistant Examiner*—Bernard Dentz

*Attorney, Agent, or Firm*—Theodore O. Groeger

[57] ABSTRACT

Compounds of the formula

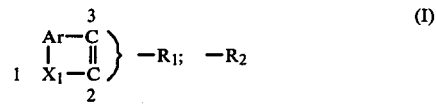

in which Ar represents optionally substituted 1,2-phenylene, $X_1$ represents oxygen or sulphur, $R_1$ represents the radical of the formula

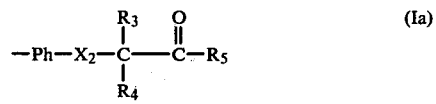

in which Ph represents optionally substituted phenylene, $X_2$ represents oxygen or sulphur, $R_3$ and $R_4$ independently of one another denote hydrogen or alkyl and $R_5$ represents optionally etherified hydroxyl or optionally substituted amino and in which $R_2$ denotes hydrogen, lower alkyl or the radical of the formula Ia and one of the groups $R_1$ and $R_2$ takes up the 2-position and the other takes up the 3-position, and salts of such compounds having salt-forming groups, e.g. ethyl 2-[4-(2-benzofuranyl)-phenoxy]-heptanoate. These compounds may be used as fibrinolytic and thrombolytic agents.

12 Claims, No Drawings

ALKANECARBOXYLIC ACID COMPOUNDS WHICH HAVE BENZOFURANYL OR BENZOTHIENYL SUBSTITUENTS

This is a continuation of application Ser. No. 798,272, filed on May 19, 1977 (now abandoned).

The invention relates to alkanecarboxylic acid compounds which have heterocyclic substituents and in particular to phenoxy- and phenylmercapto-alkanecarboxylic acid compounds of the general formula

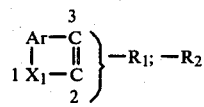
(I)

in which Ar represents optionally substituted 1,2-phenylene, $X_1$ represents oxygen or sulphur, $R_1$ represents the radical of the formula

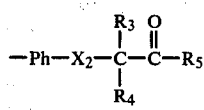
(Ia)

in which Ph represents optionally substituted phenylene, $X_2$ represents oxygen or sulphur, $R_3$ and $R_4$ independently of one another denote hydrogen or alkyl and $R_5$ represents optionally etherified hydroxyl or optionally substituted amino, and in which $R_2$ denotes hydrogen, lower alkyl or the radical of the formula Ia and one of the groups $R_1$ and $R_2$ takes up the 2-position and the other takes up the 3-position, and salts of such compounds having salt-forming groups, as well as to processes for their manufacture and also to pharmaceutical formulations, which contain these new products, and their use.

The 1,2-phenylene radical Ar can be substituted and contain, preferably in its 4-position and/or 5-position, for example lower alkyl, optionally etherified or esterified hydroxyl, such as lower alkoxy or halogen, and/or trifluoromethyl.

Both $X_1$ and $X_2$ preferably denote oxygen but both, and especially $X_1$ can also be sulphur.

The phenylene radical Ph is, in particular, a 1,4-phenylene radical; it can, however, also be bonded in the 1,3-position or 1,2-position. Substituents which may be present are, for example, lower alkyl, optionally etherified or esterified hydroxyl, such as lower alkoxy or halogen, and/or trifluoromethyl.

An alkyl group $R_3$ or $R_4$ is, above all, straight-chain alkyl but can also be branched. It contains, in particular, up to 12 carbon atoms and preferably only one of the alkyl radicals $R_3$ and $R_4$ represents higher alkyl with up to 12 carbon atoms and in this case the other radical denotes hydrogen or lower alkyl with up to 7 carbon atoms. Preferably, one of the radicals $R_3$ and $R_4$ denotes alkyl with up to 12 carbon atoms, and preferably lower alkyl with up to 7 carbon atoms, and the other denotes hydrogen, or both radicals represent lower alkyl with up to 4 carbon atoms, preferably methyl.

The group $R_5$ above all represents hydroxyl, but can also represent etherified hydroxyl, such as optionally substituted lower alkoxy, cycloalkoxy, cycloalkyl-lower alkoxy, phenyl-lower alkoxy or pyridyl-lower alkoxy. Substituents of these groups, including those of lower alkoxy, are, for example, optionally etherified hydroxyl, such as lower alkoxy, and also lower alkylidenedioxy or optionally substituted amino, such as di-lower alkylamino or lower alkyleneamino, and of phenyl-lower alkoxy, and especially of the phenyl part, are, for example, lower alkyl, optionally etherified or esterified hydroxyl, such as lower alkoxy or halogen, and/or trifluoromethyl.

As optionally substituted amino, the radical $R_5$ is, inter alia, amino, lower alkylamino, di-lower alkylamino, lower alkyleneamino or hydroxyamino.

The group $R_2$ is preferably hydrogen, especially when it takes up the 3-position, or lower alkyl, especially when it takes up the 2-position. If a group $R_2$ represents the formula Ia, it is preferably identical with the group $R_1$, but can also differ from this group.

In the preceding and in the following text, "lower" is understood to mean groups or compounds which contain up to 7, and especially up to 4, carbon atoms. The groups indicated above, and also in the text which follows, have the following further meanings:

Alkyl with up to 12 carbon atoms is, for example, n-octyl, n-nonyl, n-decyl, n-undecyl or n-dodecyl but above all denotes lower alkyl with up to 7 carbon atoms, for example methyl, ethyl, n-propyl, isopropyl, n-butyl, isobutyl, tert.-butyl, n-pentyl, isopentyl, neopentyl, n-hexyl or n-heptyl.

Lower alkoxy is, for example, methoxy, ethoxy, n-propoxy, isopropoxy, n-butoxy or isobutoxy.

Halogen is above all halogen with an atomic number of up to 36, that is to say fluorine, chlorine or bromine.

Cycloalkoxy preferably contains 3 to 8, and especially 5 or 6, carbon atoms and is, for example, cyclopentyloxy or cyclohexyloxy: cycloalkyl-lower alkoxy is, accordingly, for example cyclopropylmethoxy or cyclohexylmethoxy.

Phenyl-lower alkoxy is, for example, benzyloxy and also 1- or 2-phenylethoxy.

Pyridyl-lower alkoxy is in particular pyridylmethoxy, for example 2-, 3- or 4-pyridylmethoxy, or corresponding pyridylethoxy.

In substituted lower alkoxy, the substituent is preferably separated from the oxygen or the alkoxy group by at least 2 carbon atoms. Corresponding groups are, in particular, hydroxy-lower alkoxy, for example 2-hydroxyethoxy or 2,3-dihydroxypropoxy, lower alkoxy-lower alkoxy, for example 2-methoxyethoxy, lower alkylidenedioxy-lower alkoxy, for example 2,3-methylenedioxy-propoxy or 2,3-isopropylidenedioxy-propoxy, di-lower alkylamino-lower alkoxy, for example 2-dimethylaminoethoxy, 2-diethylaminoethoxy or 3-dimethylaminopropoxy, or lower alkyleneamino-lower alkoxy, for example 2-piperidinoethoxy.

Lower alkylamino is, for example, methylamino or ethylamino, whilst di-lower alkylamino is, for example, dimethylamino or diethylamino.

Lower alkyleneamino is, for example, pyrrolidino or piperidino.

Salts, especially pharmaceutically usable salts, of compounds of the formula I having salt-forming groups are, above all, those of compounds of this type, in which $R_5$ represents hydroxyl, with bases, such as metal salts, especially alkali metal salts or alkaline earth metal salts, for example sodium salts, potassium salts or calcium salts, or ammonium salts, for example with ammonia, optionally substituted lower alkylamines, such as lower alkylamines containing hydroxyl, such as ethanolamine, di-2-hydroxyethylamine, trimethylamine or triethylamine, or lower alkyleneamines, for example piperidine. Salts of compounds of the formula I having basic groups are acid addition salts with inorganic or organic acids, such as hydrochloric acid, sulphuric acid, maleic acid or methane-sulphonic acid.

If they contain asymmetric groupings or carbon atoms, the compounds of the present invention can be in the form of mixtures of isomers, especially racemates, or pure isomers, for example antipodes.

The compounds of the present invention possess valuable pharmacological properties. Thus, they effect, for example, an activation or normalisation of fibrinolysis, as can be shown, for example, by shortening of the euglobulin clotting time in normal rats by the method described by Rüegg et al. in Pharmacology, volume 4, page 242 (1970) or by the normalisation of the pathologically prolonged euglobulin clotting time in rats in the kaolin paw oedema test analogously to the method described by Rüegg and Jaques in Proc. Synthetic Fibrinolytic and Thrombolytic Agents, page 410 (editors Kaulla and Davidson; Chas. Thomas Publ., Springfield, Ill., 1975), on oral administration in doses of about 3 to about 30 mg/kg. Furthermore, they effect a lowering of the cholesterol and triglyceride concentration in the serum when they are administered, for example perorally in doses of about 10 to about 100 mg/kg, to male rats over a period of 4 days. In this test, the serum lipids are extracted by the method of Folch et al., J. Biol. Chem., volume 226, page 497 (1957); the cholesterol content is determined by the method of Block et al., Automation in der analytischen Chemie (Automation in analytical chemistry), page 970 (Technikon, Frankfurt a.M.; 1965) and the triglyceride content is determined by the method of Kessler and Lederer, Automation in der analytischen Chemie (Automation in analytical chemistry), page 863 (Technikon, Frankfurt a.M; 1965). Moreover, they provide protection against pulmonary embolism, as can be shown with the aid of a test method which is carried out analogously to the method of Silver et al., Science, volume 183, page 1,085 (1974) and in particular on rabbits, to which from about 10 to about 300 mg/kg of the new compounds are administered orally and which are then treated intravenously with arachidonic acid which, when administered on its own, has a lethal effect within minutes. It has also been found that the rate of side effects induced by the new compounds is low; thus, for example, the enlargement of the liver with the compounds is less than with comparable formulations.

The new compounds of the present invention can therefore correspondingly be used as fibrinolytic agents and thrombolytic agents, for example in place of anticoagulants, for normalising the fibrinolytic system and in the case of thrombo-embolic complications, and also as hypolipaemic agents for lowering the cholesterol and triglyceride content in the blood.

The invention relates in particular to compounds of the formula I in which Ar represents 1,2-phenylene which is optionally substituted, for example by lower alkyl, lower alkoxy, halogen and/or trifluoromethyl, $X_1$ represents oxygen or sulphur and $R_1$ denotes the group of the formula Ia, in which Ph represents phenylene which is optionally substituted, for example by lower alkyl or halogen, and in particular corresponding 1,4- or 1,3-phenylene, $X_2$ above all denotes oxygen, as well as sulphur, $R_3$ and $R_4$ independently of one another represent hydrogen or alkyl with up to 12 carbon atoms and $R_5$ represents hydroxyl or optionally hydroxyl-substituted lower alkoxy, phenol-lower alkoxy or pyridyl-lower alkoxy and also represents amino or hydroxyamino and $R_2$ above all denotes hydrogen or lower alkyl, the latter preferably being in the 2-position, or also represents the radical of the formula Ia, in which Ph, $X_2$, $R_3$, $R_4$ and $R_5$ have the above meanings, or salts, especially pharmaceutically usable salts, of such compounds, in which $R_5$ represents hydroxyl or pyridyl-lower alkoxy.

The invention relates above all to compounds of the formula I in which Ar represents 1,2-phenylene which is optionally substituted by lower alkyl, lower alkoxy and/or halogen, it being possible for one or more, for example two, identical or different substituents optionally to be present, $X_1$ denotes oxygen and also sulphur and $R_1$ represents the group of the formula Ia, in which Ph represents 1,4- or 1,3-phenylene, $X_2$ above all denotes oxygen and also sulphur, $R_3$ denotes alkyl with up to 12 carbon atoms, and preferably alkyl with up to 7 carbon atoms, and also hydrogen, $R_4$ represents hydrogen or lower alkyl with up to 7 carbon atoms and $R_5$ in particular represents hydroxyl and also optionally hydroxy-substituted lower alkoxy, as well as pyridyl-lower alkoxy and $R_2$ in particular represents hydrogen, as well as lower alkyl, the latter being, in particular, in the 2-position, and also represents a group of the formula Ia, in which Ph, $X_2$, $R_3$, $R_4$ and $R_5$ have the above meanings, or salts, especially pharmaceutically usable salts, of such compounds, in which $R_5$ represents hydroxyl.

The invention relates above all to compounds of the formula I in which Ar denotes, 1,2-phenylene which is optionally substituted by lower alkyl, for example methyl, and/or halogen with an atomic number of up to 36, for example fluorine, chlorine or bromine, it being possible for one or two identical or different substituents to be present, these substituents preferably occupying the 4-position and/or 5 -position of the 1,2-phenylene radical, $X_1$ is oxygen and also sulphur and $R_1$ denotes the group of the formula Ia, in which pH represents 1,4- or 1,3-phenylene, $X_2$ represents oxygen, $R_3$ represents lower alkyl with up to 7 carbon atoms, preferably in a straight chain, for example methyl, n-butyl, n-pentyl, n-hexyl or n-heptyl, as well as hydrogen, $R_4$ denotes hydrogen or lower alkyl, for example methyl, and $R_5$ represents hydroxyl and also lower alkoxy, for example methoxy or ethoxy, as well as pyridyl-lower alkoxy, such as pyridyl-methoxy, for example 3-pyridylmethoxy, and $R_2$ denotes hydrogen, as well as lower alkyl in the 2-position and also denotes a group of the formula Ia in which Ph, $X_2$, $R_3$, $R_4$ and $R_5$ have the above meanings, or salts, especially pharmaceutically usable salts, of such compounds, in which $R_5$ represents hydroxyl.

The invention relates above all to compounds of the formula I, in which Ar represents 1,2-phenylene which is optionally substituted by lower alkyl, for example methyl, and/or halogen with an atomic number of up to 36, for example fluorine or chlorine, it being possible for one or two identical or different substituents to be present, for example in the 4-position and/or 5-position of the 1,2-phenylene radical, and $X_1$ is oxygen and also sulphur, $R_1$ represents the group of the formula Ia, in which Ph represents 1,4- or 1,3-phenylene, $X_2$ is oxygen, $R_3$ is straight-chain lower alkyl with up to 7 carbon atoms, for example methyl or n-pentyl, $R_4$ denotes hydrogen or lower alkyl with up to 4 carbon atoms, for example methyl, and $R_5$ represents hydroxyl, as well as lower alkoxy, for example methoxy or ethoxy, and also pyridylmethoxy, for example 3-pyridylmethoxy, and the group $R_1$ preferably takes up the 2-position but can also be in the 3-position and $R_2$ preferably represents hydrogen and takes up the 3-position or represents lower alkyl, for example methyl, and takes up the 2-position, as well as salts, especially pharmaceutically usable salts, and in particular alkali metal salts, of such compounds, in which $R_5$ represents hydroxyl.

The invention relates above all to the compounds of the formula I in which Ar is 1,2-phenylene which is optionally substituted by lower alkyl, for example methyl, and/or halogen with an atomic number of up to 36, for example fluorine or chlorine, one or two identical or different substituents taking up the 4-position and/or the 5-position of the 1,2-phenylene radical, $X_1$ represents oxygen and $R_1$ represents the group of the formula Ia and is in the 2-position and in this group Ph is 1,4-phenylene, $R_3$ is straight-chain lower alkyl with up to 7 carbon atoms, for example methyl or n-pentyl, $R_4$ denotes hydrogen or lower alkyl with up to 4 carbon atoms, for example methyl, and $R_5$ in particular is hydroxyl and lower alkoxy, for example methoxy or ethoxy and $R_2$ represents hydrogen in the 3-position, as well as salts, especially pharmaceutically usable salts and above all alkali metal salts, of such compounds, in which $R_5$ represents hydroxyl.

The invention relates above all to the compounds of the formula I in which Ar represents 1,2-phenylene which is optionally substituted by lower alkyl, for example methyl, and/or halogen with an atomic number of up to 36, for example fluorine or chlorine, one or two identical or different substituents taking up the 4-position and/or the 5-position of the 1,2-phenylene radical, $X_1$ represents oxygen and $R_1$ represents the group of the formula Ia and is in the 2-position and in this group Ph is 1,3-phenylene, $R_3$ is straight-chain lower alkyl with up to 7 carbon atoms, for example methyl or n-pentyl, $R_4$ denotes hydrogen or lower alkyl with up to 4 carbon atoms, for example methyl, and $R_5$ in particular is hydroxyl and also lower alkoxy, for example methoxy or ethoxy, and $R_2$ represents hydrogen in the 3-position, as well as salts, especially pharmaceutically usable salts and above all alkali metal salts, of such compounds, in which $R_5$ represents hydroxyl.

In particular, the invention relates to the compounds described in the examples.

The new compounds of the formula I can be manufactured according to methods which are in themselves known.

Thus, for example, they can be obtained when a compound of the formula

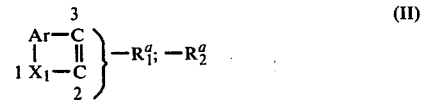

in which $R_1^a$ denotes the group of the formula —Ph—$X_2$—H (IIa) and $R_2^a$ represents $R_2$ or the radical of the formula IIa and one of the radicals $R_1^a$ and $R_2^a$ is in the 2-position and the other is in the 3-position, or a salt thereof, is reacted with a compound of the formula

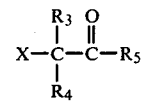

in which X denotes a reactive esterified hydroxyl, and, if desired, a compound of the formula I is converted into another compound of the formula I and/or a resulting salt is converted into the free compound or into another salt, or a resulting compound having a salt-forming group is converted into a salt and/or a mixture of isomers is separated into the isomers.

Salts of compounds of the formula II are, in particular, metal salts, especially alkali metal salts, such as sodium salts or potassium salts.

A reactive esterified hydroxyl group X is, in particular, a hydroxy group esterified with a strong acid, such as a strong mineral acid, especially a hydrogen halide acid, for example hydrochloric acid or hydrobromic acid, or sulphuric acid, or a strong organic sulphonic acid, such as a lower alkanesulphonic acid or benzenesulphonic acid, for example methanesulphonic acid, ethanesulphonic acid or p-toluenesulphonic acid. The group X is therefore above all halogen, for example chlorine or bromine, or organic sulphonyloxy, for example methylsulphonyloxy or 4-methylphenylsulphonyloxy.

The reaction is preferably carried out in the presence of an optionally salt-forming, basic agent, such as of an alkali metal carbonate, hydroxide, amide or hydride or alkaline earth metal carbonate, hydroxide, amide or hydride, for example potassium carbonate (potash), sodium hydroxide, sodium amide or sodium hydride, and of a suitable solvent or diluent, such as a lower alkanone, preferably in an anhydrous medium and, if necessary, at elevated temperature, for example at temperatures of about 40° to about 120° C., in a closed vessel and/or in an inert gas atmosphere.

In a starting material of the formula II in which $R_2^a$ represents the radical of the formula IIa, this radical is at the same time converted into the group of the formula Ia.

The starting materials of the formulae II and III are known or can be manufactured according to methods which are in themselves known.

Thus, compounds of the formula II, in which $R_2^a$ represents hydrogen or lower alkyl (the latter being in the 2-position of the benzofurane or benzo[b]thiophene ring) or also represents the group of the formula IIa, can be obtained, for example, by reacting a compound of the formula H—Ar—$X_1$—H (IV), or a salt thereof, for example an alakli metal salt thereof, with a compound of the formula $X_o$—CH($R_2^a$)—C(=O)—Ph—$X_2$—R° (V), in which $X_o$ represents halogen, especially bromine, or, if $R_2^a$ denotes the group of the formula IIa, also represents hydroxyl, and R° a radical which etherifies the hydroxyl or mercapto group, for example lower alkyl, especially methyl, preferably in the presence of an acid condensing agent, such as polyphosphoric acid or sulphuric acid, for example 70% strength sulphuric acid, and at elevated temperature. If $R_2^a$ represents hydrogen, it is possible, under the reaction conditions, for the radical of the formula —Ph—$X_2$—$R_o$ in a resulting intermediate product to migrate from the 3-position into the 2-position of the benzofurane or benzo[b]thiophene ring. In the resulting product, the etherified hydroxyl or mercapto group of the formula —$X_2$—$R_o$ (IVa) can be converted into the free hydroxyl or mercapto group in the customary manner, for example under acid conditions, such as on treatment with pyridine hydrochloride.

The new compounds of the present invention can also be obtained when the group $R_o$ in a compound of the formula

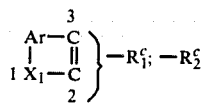 (VI)

in which $R_1^c$ denotes the group of the formula

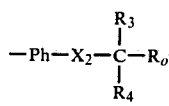 (VIa)

in which $R_o$ represents a radical which can be converted into the optionally functionally modified carboxyl group of the formula —C(=O)—$R_5$ (Ib) and $R_2^c$ represents $R_2$ or the group of the formula VIa and one of the radicals $R_1^c$ and $R_2^c$ takes up the 2-position and the other takes up the 3-position, is converted into the group of the formula —C(=O)—$R_5$ (Ib) and, if desired, the additional process measures are carried out.

A group $R_o$ is, in particular, a functionally modified carboxyl group which differs from the radical of the formula —C(=O)—$R_5$ (Ib), such as a functionally modified carboxyl group which contains the carbonyl grouping, such as a carboxyk group in the form of an anhydride, including in the form of an acid halide, for example an acid chloride, a functionally modified carboxyl group in the so-called ortho form, such as a carboxyl group which has been esterified or converted into the anhydride and is in the ortho form, for example tri-lower alkoxymethyl, such as trimethoxymethyl, or triethoxymethyl, or trihalogeno methyl, for example trichloromethyl, the cyano group or a functionally modified carboxyl group containing an imino grouping, such as a carboxyl group in the form of an iminoether, for example an imino-lower alkyl ether, or of an iminoester or amidine.

Such a group $R_o$ is converted into the desired group of the formula —C(=O)—$R_5$ (Ib) according to methods which are in themselves known, usually by means of solvolysis and especially by means of hydrolysis and also by means of alcoholysis or aminolysis.

Hydrolysis to the free carboxyl group, or if the starting material is a cyano compound, also to the carbamoyl group, can be carried out, for example, in the presence of a strong base, such as an alkali metal hydroxide, for example sodium hydroxide or potassium hydroxide, or in the presence of a strong acid, such as a mineral acid, for example hydrochloric acid or sulphuric acid.

Alcoholysis with the formation of an esterified carboxyl group, starting, above all, from acid anhydrides, such as acid halides, as well as nitriles, is carried out in the customary manner, for example by reaction with a corresponding alcohol, if necessary in the presence of acid or basic agents. If the starting compound is a cyano compound, the reaction is carried out, for example, in the presence of a mineral acid, such as sulphuric acid, and advantageously in the presence of ammonium chloride. If the starting material is an acid halide, basic agents, such as alkali metal carbonates, for example sodium carbonate or potassium carbonate, are used above all. Other acid anhydrides are converted, for example, in the presence of acid catalysts, such as sulphuric acid.

In the case of aminolysis, the starting materials are, for example, anhydrides and above all acid halides and these are reacted with ammonia or amines which contain at least one hydrogen atom on the nitrogen atom. The reaction is carried out in the customary manner, if desired in the presence of acid-binding agents, such as organic or inorganic bases.

In a starting material of the formula VI in which $R_2^c$ denotes the radical of the formula VIa, this radical is at the same time converted into the group of the formula Ia.

The starting materials of the formula VI can be manufactured in a manner which is in itself known, for example by reacting a compound of the formula II, or a salt thereof, with a compound of the formula X—C($R_3$)($R_4$)—$R_o$ (VII), in which $X_o$ represents reactive esterified hydroxyl, for example halogen, such as bromine, optionally in the presence of a condensing agent, such as of an alkali metal carbonate, and, if desired or necessary, converting a group $R_o$ into another group $R_o$.

Certain starting materials of the formula VI can also be manufactured in situ and, in particular, those starting materials of the formula VI in which $R_3$ and $R_4$ represent lower alkyl, especially methyl, and $R_o$ represents trihalogenomethyl, especially trichloromethyl, can be manufactured in this way, in particular by reacting a compound of the formula II, or a salt thereof, with a ketone of the formula $R_3$—C(=O)—$R_4$ (VIII), in which $R_3$ and $R_4$ represent lower alkyl, especially methyl, and a trihalogenomethane, especially chloroform, in the presence of a strong base, such as an alkali metal hydroxide, for example sodium hydroxide. During this reaction the starting material of the formula VI, in which $R_3$ and $R_4$ denote lower alkyl, for example methyl, and $R_o$ denotes trihalogenomethyl, for example trichloromethyl, is formed as an intermediate product, which usually is not isolated, and, under the reaction conditions, this is converted direct into a compound of the formula I in which $R_5$ represents hydroxyl. It is possible to use, for example, a suitable ketone, for example acetone, as the diluent and the reaction is preferably carried out at elevated temperature, for example at about 60° to about 120° C., if necessary in a closed vessel, and/or in an inert gas atmosphere.

The new compounds of the formula I, in which $R_1$ and optionally also $R_2$ represents a group of the formula Ia, in which at least one of the radicals $R_3$ and $R_4$ denotes hydrogen, can also be obtained when the radical $R_x$ is split off from a compound of the formula

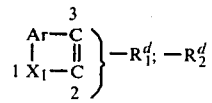 (IX)

in which $R_1^d$ represents the radical of the formula

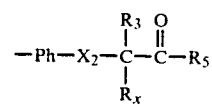 (IXa)

and $R_x$ represents a radical which an be split off, and in which one of the radicals $R_1{}^d$ and $R_2{}^d$ is in the 2-position and the other is in the 3-position and, if desired, the additional process measures are carried out.

The group $R_x$ is above all an acyl radical, such as the acyl radical of an organic, and in particular aliphatic, carboxylic acid, such as of a lower alkanecarboxylic acid, for example the acetyl radical, but above all is the acyl radical of carbonic acid or of a derivative thereof and in particular the carboxyl group.

The elimination of $R_x$ can be effected in the customary manner and in the case of the carboxyl radical is effected, for example, by heating, for example to temperatures of about 60° to about 200° C., usually in the presence of a suitable inert solvent, for example diphenyl ether, and, if necessary, in an inert gas atmosphere. The elimination of the acyl radical of a carboxylic acid, for example of the acetyl radical $R_x$, is effected, in particular, by treatment with a strong base, such as an alkali metal hydroxide, for example sodium hydroxide or potassium hydroxide, usually at elevated temperature and in the presence of a solvent or diluent.

In a starting material of the formula IX, in which $R_2{}^d$ represents a radical of the formula IXa, this radical is, during this reaction, at the same time also converted into the desired group of the formula Ia.

The starting materials of the formula IX can be manufactured, for example, by treating a compound of the formula II, or a salt thereof, with a compound of the formula

in which X represents a reactive esterified hydroxyl group, for example halogen, and $R_x{}^a$ denotes the radical $R_x$ or a radical which can be converted into this group $R_x$, for example an esterified carboxyl group, such as lower alkoxycarbonyl, and if necessary converting a group $R_x{}^a$ into the radical $R_x$, for example by hydrolysis.

The new compounds can also be obtained when a compound of the formula

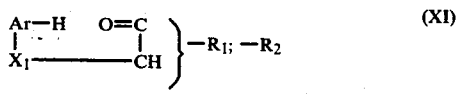

in which one of the radicals $R_1$ and $R_2$, preferably $R_1$ is a substituent on the carbonyl groups and the other is a substituent on the methylene group, is cyclised and, if desired, the additional process measures are carried out.

In a starting material of the formula XI, the group $R_1$ is preferably a substituent on the carbonyl group and $R_2$ above all represents hydrogen and also represents lower alkyl or the group of the formula Ia.

The cyclisation is usually effected in the presence of an acid condensing agent, such as of a suitable inorganic acid, for example polyphosphoric acid or sulphuric acid, and at elevated temperature, for example at about 50° to about 120° C., and in the presence of a suitable solvent or diluent, such as of an aromatic hydrocarbon, for example benzene or toluene, and, if desired or necessary, in a closed system and/or in an inert gas atmosphere.

Under the reaction conditions and especially if starting materials of the formula XI in which $X_1$ represents oxygen and $R_2$ denotes hydrogen are used, the group of the formula Ia can migrate into the 2-position. The process products obtained are thereofre, for example, compounds of the formula I in which $R_2$ denotes hydrogen and takes up the 2-position, but preferably the 3-position, or in which $r_2$ denotes lower alkyl and is a substituent in the 2-position.

The starting material of the formula XI, which usually is formed in situ, can be obtained, for example, when a compound of the formula $R_2-CH_2-C(=O)-Ph-X_2-H$ (XII), in which $R_2$ represents hydrogen or lower alkyl, or also represents a group of the formula IIa, or a salt thereof, is reacted with a compound of the formula III, in which X in particular denotes halogen, for example bromine, the methylene group in the intermediate product of the formula

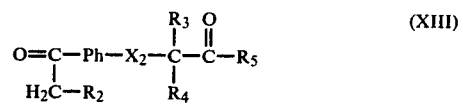

which is thus obtainable, is, for example, halogenated, for example brominated, by treatment with halogen, for example bromine, or with a N-halogeno-amide or -imide, for example N-bromosuccinimide, and the halogen compound of the formula

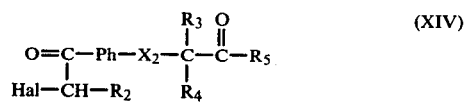

in which Hal represents halogen, especially bromine, which is thus obtainable, is reacted with a compound of the formula IV or a salt thereof.

The new compounds of the formula I, in which $X_1$ represents oxygen and $R_2$ denotes hydrogen and takes up the 3-position, can also be obtained when a compound of the formula

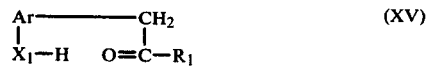

in which $X_1$ represents oxygen, is cylcised and, if desired, the additional process measures are carried out.

The cyclisation is carried out by treatment with an acid reagent, for example with an inorganic or, preferably, organic acid, such as acetic acid (usually in the form of glacial acetic acid), and at elevated temperatures, for example at about 50° to about 150° C., and, if necessary, in the presence of a solvent or diluent, in a closed vessel and/or in an inert gas atmosphere.

The starting materials of the formula XV can be manufactured, for example, when a compound of the formula $H-X_1-Ar-CHO$ (XVI), in which $X_1$ represents oxygen, is reacted, in the presence of an acid, such as hydrochloric acid, with a compound of the formula Alkyl—$CH_2$—C(=O)—$R_1$ (XVII), in which alkyl for example represents methyl or ethyl; a compound of the formula XIX is obtained, for example, by treating a compound of the formula Alkyl—$CH_2$—C(=O)—

Ph—X₂—H (XVII), in which $X_2$ has the meaning indicated above and in particular represents oxygen, with a compound of the formula III, preferably in the presence of a basic agent, such as, for example, potassium carbonate. The intermediate product of the formula

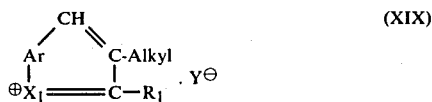

in which $Y^\ominus$ represents the anion of an acid, such as the chloride anion, which is thus obtained, can be converted, by treatment with an oxidising agent, such as hydrogen peroxide, into a compound of the formula

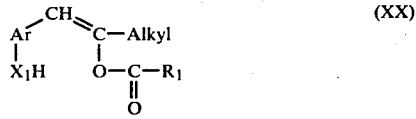

which, on treatment with a base, such as sodium hydroxide, then gives the starting material of the formula XV.

The compounds of the formula I, of the present invention, in which $X_1$ represents oxygen and $R_2$ has the meaning indicated above but preferably represents hydrogen and takes up the 3-position of the benzofurane ring, can also be obtained when $Ar_o$ in a compound of the formula

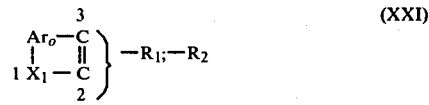

in which $Ar_o$ represents optionally substituted 3,4,5,6-tetrahydro-1,2-phenylene, $X_1$ represents oxygen and one of the radicals $R_1$ and $R_2$ takes up the 2-position and the other takes up the 3-position, is dehydrogenated to give optionally substitued 1,2-phenylene and, if desired, the additional process measures are carried out.

In a starting material of the formula XXI, $R_2$ is preferably hydrogen and $R_1$ takes up, for example, the 2-position.

The dehydrogenation of the group $Ar_o$ can be carried out in a manner which is in itself known, for example, by treatment with a dehydrogenating agent, such as an actual dehydrogenating agent, for example sulphur or selenium, or palladium in the presence of unsaturated organic compounds, such as cymene, or an inorganic or organic oxidising agent, for example manganese dioxide, or optionally suitably substituted quinone, such as tetrachlorobenzoquinone or dichlorodicyanobenzoquinone. These agents are normally used in the presence of diluents or solvents and, if desired or necessary, the reaction is carried out with cooling or warming, for example in a temperature range of about 0° C. to about 150° C., in a closed vessel and/or in an inert gas atmosphere.

The starting materials of the formula XXI can be manufactured in a manner which is in itself known, for example by reacting an enamine of the formula H—A—$r_o$—Am (XXII), in which Am represents a tertiary amino group, such as alkyleneamino and especially pyrrolidino, with a compound of the formula XVI and cyclising the resulting intermediate product by treatment with an acid, for example hydrochloric acid.

Resulting compounds of the formula I can be converted into other compounds of the present invention according to methods which are in themselves known.

Thus, for example, in resulting compounds of the formula I, free, esterified and amidated carboxyl groups of the formula Ib can be converted into one another.

Esters and amides of the formula I can be converted into free acids of the formula I in the customary manner, for example by hydrolysis, preferably in the presence of strong bases, such as an alkali metal hydroxide, for example sodium hydroxide, or strong acids, for example mineral acids. If desired, oxidising agents, such as nitrous acid, can be added during the hydrolysis of carbonyl groups.

Acids or esters of the formula I can be converted into amides of the formula I in the customary manner, for example by reaction with ammonia or amines which contain at least one hydrogen atom on the nitrogen atom, and optional dehydration of an ammonium salt which is formed as an intermediate product.

Acids of the formula I can be esterifed, for example by reaction with a corresponding alcohol usually in the presence of an acid, such as a mineral acid, for example sulphuric acid or hydrochloric acid, or in the presence of a water-binding agent, such as dicyclohexylcarbodiimide, or by reaction with a corresponding diazo compound, for example a diazoalkene. The esterification can also be carried out by reacting a salt, preferably an alkali metal salt, of an acid of the formula I with a reactive esterified alcohol, for example a corresponding halide, such as the chloride.

Free acids of the formula I can be converted, for example, into acid anhydrides and especially into acid halides, for example by reaction with halides of phosphorus or sulphur, such as thionyl chloride or phosphorus tribromide, or with suitable acid halides, such as oxalyl chloride. The acid anhydrides, and especially the acid halides, can then be converted into esters or amides, for example by reaction with corresponding alcohols, if desired in the presence of acid-binding agents, such as organic or inorganic bases, and also alcoholate compounds, for example alkali metal alcoholate compounds, or by treatment with ammonia or suitable amines In an analogous manner, resulting esters can be transesterified to other esters, for example by reaction with an alcohol, if desired in the presence of basic or acid agents, for example of a corresponding alcoholate or of a suitable mineral acid.

In resulting esters in which the alcoholic component contains adjacent hydroxyl groups, these groups can be acetalised or ketalised, for example by treatment with aldehyde or ketone, such as a lower alkanal or lower alkanone, optionally in the presence of an acid reagent, such s of a mineral acid or organic sulphonic acid. Conversely, it is possible, in resulting esters in which adjacent hydroxyl groups are bonded by ketones or aldehydes to ketal groupings or acetal groupings, for example to lower alkylidenedioxy groups, to hydrolyse these groups, preferably in the presence of acids, for example mineral acids, and also of acetic acid.

In resulting compounds of the formula I in which at least one of the groups $R_3$ and $R_4$ represents hydrogen, the hydrogen can be replaced by alkyl.

The alkylation can be carried out in the customary manner, for example by forming an α-metal salt and subsequently reacting this with a reactive ester of an alkanol. The α-metal salt of a compound of the formula I, in which $R_5$ is preferably optionally etherified hydroxyl, can be formed in the customary manner, for example by reaction with a strong base, such as an alkali metal amide or alkali metal hydride, or with an alkali metal hydrocarbon compound or alkali metal amine compound, such as sodium amide or sodium hydride or lithium amide or lithium hydride, or diisopropylamine-lithium, phenyl-lithium or butyl-lithium, and is reacted, preferably without isolation, with the reactive ester of the alkanol. Reactive esters are, in particular, those with strong inorganic or organic acids, preferably alkyl halides, such as alkyl chlorides, alkyl bromides or alkyl iodides, dialkyl sulphates or allkyl esters of lower alkenesulphonic acids or arylsulphonic acids, such as alkyl esters of methanesulphonic acid, ethanesulphonic acid, benzenesulphonic acid, 4-bromobenzenesulphonic acid or 4-toluenesulphonic acid. Depending on the starting material and/or the reaction conditions, one, two or, if $R_2$, in a compound of the formula I, represents a group of the formula Ia, in which at least one of the radicals $R_3$ and $R_4$ denotes hydrogen, also more alkyl groups can be introduced during this reaction.

The above reactions are carried out in the customary manner in the presence of absence of diluents, condensing agents and/or catalytic agents, if necessary at reduced or elevated temperature, in a closed vessel and/or in an inert gas atmosphere.

Depending on the process conditions and starting materials, end products, which may be salt-forming, are obtained in the free form or in the form of their salts, which can be converted into one another or into other salts in the customary manner. Thus, acid end products having a free carboxyl group can be obtained in the free form or in the form of their salts with bases. Resulting free acids can be converted into salts, and above all into pharmaceutically usable salts, in the customary manner, for example by reaction with corresponding basic agents, such as alkali metal hydroxides, carbonates, bicarbonates, amides or hydrides or alkaline earth metal hydroxides, carbonates, bicarbonates, amides or hydrides or suitable alkali metal lower alkanoates or with ammonia or amines. Free acids can be liberated from salts in the customary manner, for example by reaction with acid agents. End products having a basic character can optionally be obtained in the form of their acid addition salts. Resulting salts of basic end products can be converted into the free bases in a manner which is in itself known, for example by treatment with alkalis, for example alkali metal hydroxides or basic ion exchangers. The free bases can be converted into salts by reaction with organic or inorganic acids, especially those which are suitable for forming pharmaceutically usable salts.

These and other salts can also be used to purify the new compounds, for example by converting the free compounds into their salts, isolating these and reconverting them into the free compounds. Because of the close relationships between the new compounds in the free form and in the form of their salts, the free compounds, in the preceding and following text, are, where appropriate, also to be understood to include the corresponding salts in respect of general sense and intended use.

Depending on the choice of the starting materials and procedures and depending on the number of asymmetric carbon atoms, the new compounds can be in the form of optical antipodes or racemates or of mixtures of isomers (for example mixtures of racemates).

Resulting mixtures of isomers (mixtures of racemates) can be separated in a known manner into the two stereoisomeric (diastereoisomeric) pure isomers (for example racemates) on the basis of the physico-chemical differences between the constituents, for example by chromatography and/or fractional crystallisation. Advantageously, the more active of the isomers is isolated.

Resulting racemates can be resolved into the optical antipodes according to known methods, for example by recrystallisation from an optically active solvent, or with the aid of micro-organisms. By reacting a racemic free acid of the formula I with an optically active base which is able to form salts with the racemic acid and separating the salt mixture, obtained in this way, for example on the basis of the different solubilities of the components, into the diastereomers, it is possible to liberate the antipodes from these diastereomers, for example by the action of suitable basic agents. Examples of optically active bases are the D- and L-form of cinchonine, brucine, α-methyl-benzylamine, α-methyl-phenylethylamine or 1-methyl-hexylamine.

Resulting racemates of basic compounds of formula I can correspondingly be resolved into the optical antipodes by using, for example, the D- and L-forms of tartaric acids, malic acid, mandelic acid, comphersulphonic acid or quinic acid as salt-forming, optically active acids.

Preferably, the more active of two antipodes is isolated.

The invention also relates to those embodiments of the process according to which a compound obtainable as an intermediate product at any stage of the process is used as the starting material and the missing process steps are carried out, or in which a starting material is formed under the reaction conditions, or in which a reactant is optionally employed in the form of its derivatives, such as its salts, and/or in the form of mixtures of isomers or of pure isomers, such as racemates or optical antipodes.

Appropriately, the starting materials used for carrying out the reactions according to the invention are those which lead to the groups of end products mentioned in particular initially and above all to the end products which have been specifically described or singled out.

The present invention also relates to pharmaceutical formulations which contain compounds of the formula I or pharmaceutically usable salts of such compounds having salt-forming groups. The pharmaceutical formulations according to the invention are those which are intended for enteral, such as oral or rectal, as well as parenteral administration to warm-blooded animals and which contain the pharmacological active compound on its own or together with an excipient which can be used pharmaceutically. The dosage of the active compound depends on the species of warm-blooded animal, the body weight and age and on the state of health of the individual patient, as well as on the mode of administration. On average, a daily dose of about 150 to about 750 mg of active compound is administered to a warm-blooded animal which has a body weight of about 70 kg.

The new pharmaceutical formulations contain from about 10% to about 95%, and preferably from about 20% to about 90%, of the active compound. Pharmaceutical formulations according to the invention can be in the form of dosage units, such as dragées, tablets, capsules, suppositories or ampoules.

The pharmaceutical formulations of the present invention are manufactured in a manner which is in itself known, for example by means of conventional mixing, granulating, dragée-making, dissolving or lyophilising processes. Thus, pharmaceutical formulations for oral use can be obtained by combining the active compound with solid excipients, optionally granulating a resulting mixture and processing the mixture or granules, after adding suitable auxiliaries if desired or necessary, to give tablets or dragée cores.

Suitable excipients are, in particular, fillers, such as sugars, for example lactose or sucrose, mannitol or sorbitol, cellulose formulations and/or calcium phosphates, for example tricalcium phosphate or calcium hydrogen phosphate, as well as binders, such as starch pastes using, for example, maize starch, wheat starch, rice starch or potato starch, gelatine, tragacanth, methylcellulose, hydroxypropyl-methylcellulose, sodium carboxymethylcellulose and/or polyvinylpyrrolidone, and/or, if desired, disintegrating agents, such as the abovementioned starches, and also carboxymethylstarch, crosslinked polyvinylpyrrolidone, agar or alginic acid or a salt thereof, such as sodium alginate. Auxiliaries are, above all, flow regulating agents and lubricants, for example silica, talc, stearic acid or salts thereof, such as magnesium stearate or calcium stearate, and/or polyethylene glycol. Dragée cores are provided with suitable coatings, which, if desired, are resistant to gastric juices, and for this purpose, inter alia, concentrated sugar solutions, which optionally contain gum arabic, talc, polyvinylpyrrolidone, polyethylene glycol and/or titanium dioxide, lacquer solutions in suitable organic solvents or solvent mixtures, or, in order to produce coatings resistant to gastric juices, solutions of suitable cellulose formulations, such as acetylcellulose phthalate or hydroxypropylmethylcellulose phthalate, are used. Dyestuffs or pigments can be added to the tablets or dragée coatings, for example for identification or in order to charactrise different doses of active compound.

Other pharmaceutical formulations which can be used orally are push-fit capsules made of gelatine, as well as soft, sealed capsules made of gelatine and a plasticiser, such as glycerol or sorbitol. The push-fit capsules can contain the active compound in the form of granules, for example mixed with fillers, such as lactose, binders, such as starches and/or lubricants, such as talc or magnesium stearate, and, optionally, stabilisers. In soft capsules, the active compound is preferably dissolved or suspended in suitable liquids, such as fatty oils, liquid paraffin or liquid polyethylene glycols, and it is also possible to add stabilisers.

Possible pharmaceutical formulations which can be used rectally are, for example, suppositories, which consist of a combination of the active compound with a suppository base. Suitable suppository bases are, for example, natural or synthetic triglycerides, paraffin hydrocarbons, polyethylene glycols or higher alkanols. In addition it is also possible to use gelatine rectal capsules which consist of a combination of the active compound with a base; examples of base materials which can be used are liquid triglycerides polyethylene glycols or paraffin hydrocarbons.

Formulations suitable for parenteral administration are, above all, aqueous solutions of an active compound in a water-soluble form, for example of a water-soluble salt, and also suspensions of the active compound, such as corresponding oily injection suspensions, for which suitable lipophilic solvents or vehicles, such as fatty oils, for example sesame oil, or synthetic fatty acid esters, for example ethyl oleate or triglycerides, are used, or aqueous injection suspensions, which contain substances which increase the viscosity, for example, sodium carboxymethylcellulose, sorbitol and/or dextran and, optionally, also stabilisers.

The invention also comprises the use of the compounds of the formula I, or of pharmaceutically usable salts of such compounds having salt-forming groups, as substances which have a pharmacological action and especially as thrombolytic agents and also as hypocholesterolemic agents, preferably in the form of pharmaceutical formulations.

The examples which follow illustrate the invention described above; however, they are not intended to restrict the scope of the invention in any way. Temperatures are given in degrees Centigrade.

EXAMPLE 1

44.5 g of 2-(4-hydroxyphenyl)-benzofurane and 38.2 g of potassium carbonate are heated in 850 ml of ethyl methyl ketone to 35°, under nitrogen. 60.2 g of ethyl 2-bromoheptanoate are then added dropwise, whilst stirring, and the mixture is then heated under reflux for 20 hours, whilst stirring vigorously. The reaction mixture is then cooled to 60° and filtered at this temperature. The residue is rinsed in portions with 1 liter of ethyl acetate. The combined filtrates are washed with three times 1 liter of water and dried over sodium sulphate and the solvent is removed in vacuo. The residue is then freed from volatile constituents by heating to 100° under a high vacuum for 2 hours, dissolved in a little methylene chloride and chromatographed over 500 g of alumimium oxide (activity II, neutral). The first fraction eluted with 2 liters of methylene chloride is ethyl 2-[4-(2-benzofuranyl)-phenoxy]-heptanoate which, after recrystalisation from hexane, melts at 66.5°–67.5°.

EXAMPLE 2

19.0 g of ethyl 2-[4-(2-benzofuranyl)-phenoxy]-heptanoate are dissolved in 650 ml of ethyl alcohol and the solution is rendered alkaline with 190 ml of 2 N sodium hydroxide solution. The reaction solution is stirred at a temperature of 40° for 20 hours, under nitrogen. The ethyl alcohol is then evaporated in vacuo, the pH of the residual aqueous solution is adjusted to 0 to 1 by adding 2 N hydrochloric acid and the solution is extracted with twice 350 ml of ethyl acetate. The combined organic phases are dried over sodium sulphate and filtered and the filtrate is evaporated in vacuo. After recrystallisation from cyclohexane, the pure 2-[4-(2-benzofuranyl)-phenoxy]-heptanoic acid melts at 140°–141°.

EXAMPLE 3

17.3 g of 2-[4-hydroxyphenyl]-benzofurane and 15.2 g of anhydrous potassium carbonate are heated in 350 ml of methyl ethyl ketone to 35°, under nitrogen. 18.1 g of ethyl 2-bromopropionate are then added dropwise, whilst stirring, and subsequently the mixture is heated under reflux for 20 hours, whilst stirring vigorously. The reaction mixture is then cooled to 50° and filtered at this temperature. The residue is rinsed with 1 liter of ethyl acetate. The combined filtrates are washed with three times 1 liter of water and dried over sodium sulphate and the solvent is evaporated in vacuo. After recrystallisation from hexane, the ethyl 2-[4-(2-benzofuranyl)-phenoxy]-propionate melts at 60.5 to 62.0°.

EXAMPLE 4

12.0 g of ethyl 2-[4-(2-benzofuranyl)-phenoxy]-propionate are dissolved in 400 ml of ethyl alcohol and the solution is rendered alkaline by the addition of 120 ml of 2 N sodium hydroxide solution. The solution is stirred for 20 hours under nitrogen and at a temperature of 40°. The ethyl alcohol is then evaporated in vacuo, the pH of the residual aqueous phase is adjusted to 0 to 1 by adding 2 N hydrochloric acid and the solution is extracted with twice 300 ml of ethyl acetate, the combined organic phases are washed once more with 500 ml of water, dried over sodium sulphate and filtered and the filtrate is evaporated in vacuo. The 2-[4-(2-benzofuranyl)-phenoxy]-propionic acid is recrystallised from toluene and then melts at 188°–190°.

EXAMPLE 5

25.4 g of 2,3-di-(4-hydroxyphenyl)-5,6-dimethylbenzofurane and 40.4 g of anhydrous potassium carbonate are heated in 350 ml of methyl ethyl ketone to 35°, under nitrogen. 54.0 g of ethyl 2-bromopropionate are then added dropwise, whilst stirring, and subsequently the mixture is heated under reflux for 66 hours. The reaction mixture is then cooled to 50° and filtered at this temperature. The filter residue is rinsed with 1 liter of ethyl acetate and the combined filtrates are washed with five times 500 ml of water and dried over sodium sulphate and the solvent is removed in vacuo. The residue is then freed from readily volatile constituents by heating to 120° for 3 hours under a high vacuum. The residue is dissolved in a little methylene chloride and chromatographed on 500 g of aluminium oxide (activity II, neutral). The first fraction eluted with 1.5 liters of methylene chloride is 2,3-di-[4-(1-ethoxycarbonylethoxy)-phenyl]5,6-dimethylbenzofurane which has a boiling point 0.3 mm Hg of 120°.

The starting material can be prepared as follows:

160 g of 73% strength aqueous sulphuric acid are added dropwise to a mixture of 54.5 g of 1,2-di-(4-methoxyphenyl)-2-oxo-ethanol (p-anisoin) and 73 g of 3,4-dimethylphenol and the mixture is heated at 130°–135° for 20 minutes and then cooled to 20°. The reaction mixture is rendered alkaline by adding an aqueous solution of sodium hydroxide and is heated under reflux and then cooled. It is extracted twice with ethyl acetate; the combined organic extracts are washed with a 2 N aqueous solution of sodium hydroxide and with water, dried over sodium sulphate and filtered and the filtrate is concentrated to half its volume and cooled. The crystalline precipitate is filtered off and recrystallised from ethyl acetate and gives 2,3-di-(4-methoxyphenyl)-5,6-dimethylbenzofurane, melting point 153°.

A mixture of 10 g of 2,3-di-(4-methoxyphenyl)-5,6-dimethyl-benzofurane and 50 g of pyridine hydrochloride is heated at 210° for 2½ hours, whilst stirring and under a nitrogen atmosphere. The reaction mixture is coled to 100° and, at this temperature, is poured into 250 ml of 6 N hydrochloric acid, whilst stirring. The crystalline precipitate is filtered off and recrystallised from chloroform; this gives 2,3-di-(4-hydroxyphenyl)-5,6-dimethyl-benzofurane, melting point 195°–196°.

EXAMPLE 6

24.0 g of 2,3-di-[4-(1-ethoxycarbonylethoxy)-phenyl]-5,6-dimethyl-benzofurane are dissolved in 1.5 liters of ethyl alcohol and the solution is rendered alkaline by adding 480 ml of 2 N sodium hydroxide solution. The solution is stirred at a temperature of 40° for 20 hours. The ethyl alcohol is then evaporated in vacuo, the pH of the residual aqueous solution is adjusted to 0 to 1 by adding 2 N hydrochloric acid and the solution is extracted with twice 500 ml of ethyl acetate. The combined organic phases are washed with a further three times 500 ml of water, dried over sodium sulphate and filtered and the filtrate is evaporated. After recrystallisation from ethyl acetate/cyclohexane, the 2,3-di-[4-(1-carboxyethoxy)-phenyl]-5,6-dimethyl-benzofurane melts at 183°–185° C.

EXAMPLE 7

8.3 g of 2-methyl-3-[4-hydroxyphenyl]-benzofurane and 6.5 g of anhydrous potassium carbonate in 200 ml of ethyl methyl ketone are warmed to 35°, under nitrogen. 10.7 g of ethyl 2-bromo-heptanoate are then added slowly dropwise and the mixture is subsequently heated under reflux for 20 hours, whilst stirring vigorously. The reaction mixture is cooled to 50° and filtered at this temperature. The filter residue is rinsed with 800 ml of ethyl acetate. The combined organic phases are washed with three times 1 liter of water, dried over sodium sulphate and filtered and the filtrate is evaporated in vacuo. The residue is subjected to fractional distillation under a high vacuum. The fraction which passes over at 180° and 0.2 mm Hg is ethyl 2-[4-(2-methyl-3-benzofuranyl)-phenoxy]-heptanoate.

EXAMPLE 8

10.0 g of ethyl 2-[4-(2-methyl-3-benzofuranyl)-phenoxy]-heptanoate are dissolved in 200 ml of ethyl alcohol and the solution is rendered strongly alkaline by adding 80 ml of 2 N sodium hydroxide solution. The solution is stirred at a temperature of 40° for 20 hours, under nitrogen. The ethyl alcohol is then evaporated in vacuo, the pH of the residual aqueous phase is adjusted to 0 to 1 by adding 2 N hydrochloric acid and the solution is extracted with three times 300 ml of diethyl ether. The combined organic phases are washed twice more with 500 ml of water in each case, dried over sodium sulphate and filtered and the filtrate is evaporated in vacuo. The residual oil is dissolved in 30 ml of methyl alcohol, the solution is stirred with 1 g of active charcoal for 5 minutes and the mixture is filtered with the aid of a cellulose powder formulation (Hyflo). The clear and colourless filtrate is diluted with water until it becomes slightly turbid. 2-[4-(2-Methyl-3-benzofuranyl)-phenoxy]-heptanoic acid melts at 121.5°–123°.

EXAMPLE 9

4 g of 2-methyl-3-[4-hydroxyphenyl]-benzofurane are dissolved in 50 ml of acetone and 3.5 g of sodium hydroxide are added. 2.25 g of chloroform are then added slowly dropwise and the solution is heated under reflux for 5 hours, under nitrogen and whilst stirring. It is then cooled to 10° to 15° and the crystals are filtered off. The sodium salt of 2-methyl-2-[p-(2-methyl-3-benzofuranyl)-phenoxy]-propionic acid is dissolved in 500 ml of water, the solution is filtered and the pH of the filtrate is adjusted to 0 to 1 by adding 2 N hydrochloric acid, the resulting mixture is extracted with twice 350 ml of diethyl ether, the organic phases are combined, dried over sodium sulphate and filtered and the filtrate is evaporated. After crystallization from hexane, the 2-methyl-2-[4-(2-methyl-3-benzofuranyl)-phenoxy]-propionic acid melts at 143°–144°.

EXAMPLE 10

2.5 g of 2-[4-hydroxyphenyl]-benzofurane are dissolved in 37 ml of acetone and reacted, under nitrogen, with 2.6 g of analytical grade sodium hydroxide. 1.67 g of chloroform are then added slowly dropwise and the solution is heated under reflux for 3 hours. The solution is then cooled to 10°–15° and filtered and the crystals are rinsed with 10 ml of acetone. The sodium salt of 2-methyl-2-[p-(2-benzofuranyl)-phenoxy]-propionic acid is dissolved in 500 ml of water and the solution is acidified by adding 2 N hydrochloric acid and extracted with twice 350 ml of diethyl ether. The organic phases are combined, dried over sodium sulphate and filtered and the filtrate is evaporated. After recrystallisation from ether/benzene/hexane, the 2-methyl-2-[4-(2-benzofuranyl)-phenoxy]-propionic acid melts at 179°–181°.

EXAMPLE 11

15.0 g of 2-[4-hydroxyphenyl]-5-fluorobenzofurane and 11.8 g of anhydrous potassium carbonate in 260 ml of methyl ethyl ketone are heated to 35° under nitrogen and 18.6 g of ethyl 2-bromoheptanoate are then added dropwise, whilst stirring, and subsequently the solution is heated under reflux for 20 hours. The reaction suspension is then cooled to 50° and filtered and the material on the filter is rinsed with twice 200 ml of ethyl acetate. The filtrate is now washed with three times 200 ml of water. The organic phase is dried over sodium sulphate and filtered and the filtrate is concentrated in vacuo. The residue is then freed from volatile constituents by heating at 100° for 2 hours under a high vacuum. The residual crystals are recrystallised from hexane. The ethyl 2-[4-(5-fluoro-2-benzofuranyl)-phenoxy]-heptanoate melts at 67°.

The starting material can be prepared as follows:

A mixture of 202 g of 4-methoxy-phenacyl bromide, 100 g of 4-fluorophenol and 124.6 g of potassium carbonate in 1,500 ml of anhydrous ethyl methyl ketone is heated under reflux for 5 hours under a nitrogen atmosphere and then poured into 2,500 ml of an ice/water mixture, whilst stirring. The aqueous phase is extracted with four times 250 ml of ethyl acetate and the combined organic phases are washed with 2,000 ml of water, dried over sodium sulphate and filtered and the filtrate is evaporated under reduced pressure. The residue is recrystallised from ethanol and gives 4-methoxyphenacyl 4'-fluorophenyl ether, melting point 92°–94°.

A mixture of 197 g of 4-methoxyphenacyl 4'-fluorophenyl ether and 551 g of polyphosphoric acid in 3,650 ml of xylene is heated under reflux for 8 hours, whilst stirring, and then cooled to 80°. The xylene phase is separated off at this temperature: the polyphosphoric acid phase is extracted a further twice at 80°, using 200 ml of xylene in each case. The combined organic solutions are each washed with twice 1,000 ml of water, dried over sodium sulphate and evaporated under reduced pressure. After recrystallisation from methanol, the 2-(4-methoxyphenyl)-5-fluorobenzofurane melts at 152°.

A mixture of 120 g of 2-(4-methoxyphenyl)-5-fluorobenzofurane and 426 g of pyridine hydrochloride is heated at 210° for 1½ hours under a nitrogen atmosphere and whilst stirring. The mixture is cooled to 100° and 500 ml of 6 N hydrochloric acid are added dropwise at this temperature. 2-(4-Hydroxyphenyl)-5-fluorobenzofurane separates out as a crystalline precipitate and is filtered off and washed with 500 ml of water. After recrystallising from a 9:1 mixture of hexane and isopropanol, the product melts at 204°–205° C.

EXAMPLE 12

10.0 g of ethyl 2-[4-(5-fluoro-2-benzofuranyl)-phenoxy]-heptanoate are dissolved in 350 ml of ethyl alcohol and the solution is rendered alkaline by adding 105 ml of 2 N sodium hydroxide solution. This solution is stirred at a temperature of 40° for 20 hours, under nitrogen. The ethyl alcohol is then evaporated in vacuo, the pH of the residual aqueous solution is adjusted to 0 to 1 by adding 2 N hydrochloric acid and the solution is extracted with three times 250 ml of ethyl acetate. The organic phases are twice washed with 200 ml of water, combined, dried over sodium sulphate and filtered and the filtrate is evaporated in vacuo. The 2-[4-(5-fluoro-2-benzofuranyl)-phenoxy]-heptanoic acid is recrystallised from cyclohexane and melts at 158°.

EXAMPLE 13

22 g of 2-[4-hydroxyphenyl]-5-fluorobenzofurane and 17.8 g of anhydrous potassium carbonate in 410 ml of ethyl methyl ketone are heated to 35° under nitrogen. 21.2 g of ethyl 2-bromopropionate are then added slowly dropwise and subsequently the mixture is heated under reflux for 20 hours, whilst stirring vigorously. The reaction mixture is then cooled to 50° and filtered at this temperature. The residue is rinsed with 1 liter of ethyl acetate. The combined organic phases are washed three times with 500 ml of water, dried over sodium sulphate and filtered and the solvent is removed from the filtrate in vacuo. The residue is recrystallised from hexane. Ethyl 2-[4-(5-fluoro-2-benzofuranyl)-phenoxy]-propionate melts at 95°–96°.

EXAMPLE 14

8.7 g of ethyl 2-[4-(5-fluoro-2-benzofuranyl)-phenoxy]-propionate are dissolved in 367 ml of ethyl alcohol and the solution is rendered alkaline by adding 107 ml of 2 N sodium hydroxide solution. The reaction solution is stirred at a temperature of 40° for 20 hours under nitrogen. The ethyl alcohol is then concentrated in vacuo, the pH of the residual aqueous solution is adjusted to 0 to 1 by adding 2 N hydrochloric acid and the solution is extracted with twice 350 ml of ethyl acetate. The organic solutions are twice washed with 400 ml of water, dried over sodium sulphate and filtered and the filtrate is evaporated in vacuo. After recrystallization from toluene, the 2-[4-(5-fluoro-2-benzofuranyl)-phenoxy]-propionic acid melts at 182°–184°.

EXAMPLE 15

25.0 g of 2-[4-hydroxyphenyl]-5-fluorobenzofurane and 20.2 g of anhydrous potassium carbonate in 465 ml of methyl ethyl ketone are heated to 35°, under nitrogen. 22.2 g of ethyl bromoacetate are then added slowly dropwise and the mixture is then heated under reflux for 20 hours, whilst stirring vigorously. The reaction solution is then cooled to 50° and filtered at this temperature. The filter residue is rinsed with 1 liter of ethyl acetate, the organic solutions are washed three times with 600 ml of water, combined, dried over sodium sulphate and filtered and the solvent is concentrated in vacuo. The ethyl 2-[4-(5-fluoro-2-benzofuranyl)-phenoxy]-acetate is recrystallised from n-heptane and melts at 123°–124°.

EXAMPLE 16

9.7 g of ethyl 2-[4-(5-fluoro-2-benzofuranyl)-phenoxy]-acetate are dissolved in 427 ml of ethyl alcohol and the solution is rendered alkaline by adding 124 ml of 2 N sodium hydroxide solution. The reaction solution is stirred at a temperature of 45° for 20 hours, under nitrogen. The ethyl alcohol is then concentrated in vacuo, the pH of the residual aqueous solution is adjusted to 0 by adding 2 N hydrochloric acid and the solution is twice extracted with 400 ml of ethyl acetate. The organic solutions are washed twice with 400 ml of water, dried over sodium sulphate and filtered and the filtrate is evaporated in vacuo. The 2-[4-(5-fluoro-2-benzofuranyl)-phenoxy]-acetic acid is recrystallised from 200 ml of isopropyl alcohol and melts at 209°–211°.

EXAMPLE 17

12.5 g of 2-[4-hydroxyphenyl]-benzofurane and 9.0 g of anhydrous potassium carbonate in 250 ml of methyl ethyl ketone are heated to 35°, under nitrogen. 10 g of ethyl bromoacetate are then added slowly dropwise and subsequently the mixture is heated under reflux for 27 hours, whilst stirring vigorously. It is then cooled to 60° and filtered at this temperature. The filter residue is rinsed with 850 ml of ethyl acetate. The combined filtrates was washed three times with 800 ml of water and dried over sodium sulphate and the solvent is evaporated in vacuo. The ethyl 2-[4-(2-benzofuranyl)-phenoxy]-acetate is recrystallised from cyclohexane and melts at 123°–124°.

EXAMPLE 18

6.4 g of ethyl 2-[4-(2-benzofuranyl)-phenoxy]-acetate are dissolved in 200 ml of ethyl alcohol and the solution is rendered alkaline by adding 110 ml of 2 N sodium hydroxide solution. The reaction solution is stirred at a temperature of 45° for 20 hours, under nitrogen. The ethyl alcohol is then concentrated in vacuo, the pH of the residual aqueous suspension is adjusted to 0 by adding 2 N hydrochloric acid and the mixture is extracted with twice 300 ml of ethyl acetate. The organic solutions are washed a further three times with 400 ml of water, combined, dried over sodium sulphate and filtered and the filtrate is evaporated in vacuo. The 2-[4-(2-benzofuranyl)-phenoxy]-acetic acid is recrystallised from isopropyl alcohol and melts at 207°–209°.

EXAMPLE 19

20.0 g of 2(or 3)-(4-hydroxyphenyl)-benzo[b]thiophene and 16.3 g of anhydrous potassium carbonate in 375 ml of methyl ethyl ketone are heated to 35°, under nitrogen. 19.4 g of ethyl 2-bromopropionate are then added dropwise, whilst stirring, and subsequently the mixture is heated for 20 hours under reflux and whilst stirring. The suspension is then cooled to 50° and filtered at this temperature and the material on the filter is rinsed with 1 liter of ethyl acetate. The combined filtrates are rinsed three times with 500 ml of water, dried over sodium sulphate and filtered and the solvent is evaporated in vacuo. The ethyl 2(or 3)-[4-(2-benzo[b]-thienyl)-phenoxy]-propionate is recrystallised from hexane and melts at 110°.

The starting material can be prepared as follows:

A mixture of 160 g of 4-methoxy-phenacyl bromide, 77 g of thiophenol and 96 g of potassium carbonate in 350 ml of anhydrous acetone is heated under reflux for 4 hours and then poured into 2,000 ml of an ice/water mixture. The resulting mixture is stirred for 30 minutes at 20° and the crystalline precipitate is filtered off and washed with 5,000 ml of water. After recrystallisation from ethanol, the 4-methoxyphenacyl phenyl thioether melts at 87°.

A mixture of 155 g of 4-methoxyphenacyl phenyl thioether and 465 g of polyphosphoric acid in 2,800 ml of xylene is heated under reflux for 15 hours and then cooled to 110° and the supernatant xylene phase is decanted off; the polyphosphoric acid phase is extracted a further twice at 110°, using 1,000 ml of xylene each time. The combined xylene solutions are evaporated to half their volume and then cooled to room temperature; the resulting precipitate is filtered off and recrystallised with the addition of an active charcoal formulation (Norit). The 2(or 3)-(4-methoxyphenyl)-benzo[b]thiophene thus obtained melts at 191°.

A mixture of 43 g of 2(or 3)-(4-methoxyphenyl)-benzo[b]thiophene and 160 g of pyridine hydrochloride is heated at 210° for 2 hours under a nitrogen atmosphere and then poured into 600 ml of 6 N hydrochloric acid, whilst stirring. The aqueous phase is extracted with three times 300 ml of ethyl acetate. The combined organic solutions are washed successively with twice 500 ml of 2 N hydrochloric acid and with twice 500 ml of water, dried over sodium sulphate and filtered and the filtrate is evaporated under reduced pressure. The residue is recrystallised from acetonitrile and gives 2(or 3)-(4-hydroxyphenyl)-benzo[b]thiophene, melting point 228°.

EXAMPLE 20

6.3 g of ethyl 2(or 3)-[4-(2-benzo[b]thienyl)-phenoxy]-propionate are dissolved in 272.5 ml of ethyl alcohol and the solution is rendered alkaline with 80 ml of 2 N sodium hydroxide solution. The reaction solution is stirred at a temperature of 40° for 20 hours. The ethyl alcohol is then evaporated in vacuo, the pH of the residual aqueous phase is adjusted to 0 by adding 2 N hydrochloric acid and the mixture is extracted with twice 350 ml of ethyl acetate, the combined organic phases are dried over sodium sulphate and filtered and the filtrate is evaporated in vacuo. The 2(or 3)-[4-(2-benzo[b]-thienyl)-phenoxy]-propionic acid is recrystallised from acetonitrile and melts at 220° C.

EXAMPLE 21

In an analogous manner, the following compounds: ethyl 2-[4-(2-benzofuranyl)-phenoxy]-butyrate, melting point 66°–68°, 2-[4-(2-benzofuranyl)-phenoxy]-butyric acid, melting point 173°–175°, ethyl 2-[4-(2-benzofuranyl)-phenoxy]-dodecanoate, melting point 53°–54°, 2-[4-(2-benzofuranyl)-phenoxy]-dodecanoic acid, melting point 135°–137° and 2-[4-(2-benzofuranyl)-phenoxy]-nonanoic acid, melting point 146°–148° and its ethyl ester which has a melting point of 57°–58.5°, can be prepared by suitable choice of the starting materials.

EXAMPLE 22

3-Pyridylmethyl2-[4-(2-benzofuranyl)-phenoxy]-heptanoate, melting point 91°–92°, can be obtained, for example, by treating the sodium salt of 2-[4-(2-benzofuranyl)-phenoxy]-heptanoic acid with 3-pyridyl-methyl bromide-hydrochloride.

EXAMPLE 23

In an analogous manner, the following compounds: ethyl 2-[3-(2-benzofuranyl)-phenoxy]-heptanoate, melting point 37°–38°, ethyl 2-[3-(2-benzofuranyl)-phenoxy]-propionate, boiling point 176°–177° (under 0.12 mm Hg), 2-[3-(2-benzofuranyl)-phenoxy]-heptanoic acid, in the form of the hemi-hydrate, melting point 147°–149°, 2-[3-(2-benzofuranyl)-phenoxy]-propionic acid, melting point 144°–146° and 2-methyl-2-m-(benzofuranyl)-phenoxy-propionic acid, melting point 129°–130°, can be prepared by suitable choice of the starting materials.

EXAMPLE 24

Tablets containing 0.1 g of 2-[4-(2-benzofuranyl)-phenoxy]-heptanecarboxylic acid can be prepared as follows:

| Composition (for 10,000 tablets): | |
| --- | --- |
| 2-[4-(2-Benzofuranyl)-phenoxy]-heptanecarboxylic acid | 50.00 g |
| Lactose | 670.00 g |
| Wheat starch | 205.00 g |
| Colloidal silica | 50.00 g |
| Magnesium stearate | 5.00 g |
| Talc | 20.00 g |
| Water | q.s. |

The 2-[4-(2-benzofuranyl)-phenoxy]-heptanecarboxylic acid is mixed with part of the wheat starch and with the lactose and the colloidal silica and a mixture is forced through a sieve. A further part of the wheat starch is mixed to a paste with five times the amount of water on a waterbath and the above powder mixture is kneaded with this paste until a slightly plastic mass has formed. The plastic mass is pressurized through a sieve of about 3 mm mesh width and dried and the dry granules are again forced through a sieve. The remaining wheat starch, the talc and the magnesium stearate are then mixed in and the resulting mixture is pressed to give tablets (with a breaking groove) weighing 0.1 g.

What is claimed is:

1. An alkanecarboxylic acid compound of the formula

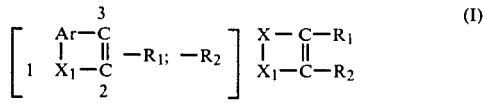

in which one of X and $X_1$ represents oxygen or sulphur, and the other represents 1,2-phenylene or 1,2-phenylene substituted by one to four identical or different members selected from the group consisting of lower alkyl, lower alkoxy, halogen and trifluoromethyl, $R_1$ represents the radical of the formula

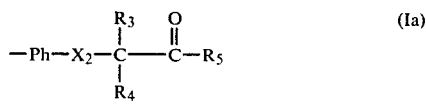

in which Ph represents 1,3- or 1,4-phenylene or such phenylene substituted as said 1,2-phenylene moiety X or $X_1$, $X_2$ represents oxygen or sulphur, $R_3$ and $R_4$ independently of one another denote hydrogen or alkyl with up to 12 carbon atoms and $R_5$ represents hydroxyl, amino, lower alkoxy, hydroxy-lower alkoxy, phenyl-lower alkoxy, pyridyl-lower alkoxy, lower alkylamino, di-lower alkylamino or hydroxylamino, and $R_2$ denotes hydrogen, lower alkyl or said radical of the formula Ia; or a pharmaceutically usable salt of said acids with $R_5$ being hydroxyl.

2. A compound according to claim 1, in which formula one of X and $X_1$ represents 1,2-phenylene or 1,2-phenylene substituted by lower alkyl, lower alkoxy and/or halogen, it being possible for one or more identical or different substituents to be present and the other of X and $X_1$, as well as $X_2$ denotes oxygen or sulphur, $R_1$ represents the group of the formula Ia, in which Ph represents 1,4-phenylene, $R_3$ denotes alkyl with up to 12 carbon atoms or hydrogen, $R_4$ represents hydrogen or alkyl with up to 7 carbon atoms, $R_5$ represents hydroxyl, lower alkoxy or pyridyl-lower alkoxy, and $R_2$ represents hydrogen, lower alkyl or said group of the formula Ia; or a pharmaceutically usable salt of said acids with $R_5$ being hydroxyl.

3. A compound according to claim 1, in which formula one of X and $X_1$ denotes 1,2-phenylene or 1,2-phenylene substituted by lower alkyl and/or halogen with an atomic number of up to 36, it being possible for one or two identical or different substituents to be present, and the other of X and $X_1$ is oxygen or sulphur, $R_1$ denotes the group of the formula Ia, in which Ph represents 1,4- or 1,3-phenylene, $X_2$ represents oxygen, $R_3$ represents alkyl with up to 7 carbon atoms or hydrogen, $R_4$ denotes hydrogen or lower alkyl, $R_5$ represents hydroxyl, lower alkoxy or pyridyl-lower alkoxy, and $R_2$ denotes hydrogen, lower alkyl in the 2-position or a group of said formula Ia; or a pharmaceutically usable salt of said acids with $R_5$ being hydroxyl.

4. A compound according to claim 1, in which formula $X_1$ represents 1,2-phenylene or 1,2-phenylene substituted by lower alkyl and/or halogen with an atomic number of up to 36, it being possible for one or two substituents to be identical or different, X is oxygen or sulphur, $R_1$ represents the group of the formula Ia, in which Ph represents 1,4- or 1,3-phenylene, $X_2$ is oxygen, $R_3$ is straight-chain alkyl with up to 7 carbon atoms, $R_4$ denotes hydrogen or alkyl with up to 4 carbon atoms, $R_5$ represents hydroxyl, lower alkoxy or pyridylmethoxy and $R_2$ represents hydrogen; or a pharmaceutically usable salt of said acids with $R_5$ being hydroxyl.

5. A compound according to claim 1, in which formula $X_1$ is 1,2-phenylene or 1,2-phenylene substituted by lower alkyl and/or halogen with an atomic number of up to 36, one or two identical or different substituents taking up the 4-position and/or the 5-position therein, X as well as $X_2$ represent oxygen, $R_1$ represents the group of the formula Ia in which Ph is 1,4-phenylene, $R_3$ is straight-chain alkyl with up to 7 carbon atoms, $R_4$ denotes hydrogen or lower alkyl with up to 4 carbon atoms, $R_5$ is hydroxyl or lower alkoxy, and $R_2$ represents hydrogen; or a pharmaceutically usable salt of said acids with $R_5$ being hydroxyl.

6. A compound according to claim 1, in which formula $X_1$ is 1,2-phenylene or 1,2-phenylene substituted by lower alkyl and/or halogen with an atomic number of up to 36, one or two identical or different substituents taking up the 4-position and/or the 5-position therein, X as well as $X_2$ represent oxygen, $R_1$ represents the group of the formula Ia in which Ph is 1,3-phenylene, $R_3$ is straight-chain alkyl with up to 7 carbon atoms, $R_4$ denotes hydrogen or alkyl with up to 4 carbon atoms, $R_5$ is hydroxyl or lower alkoxy, and $R_2$ represents hydrogen; or a pharmaceutically usable salt of said acids with $R_5$ being hydroxyl.

7. A compound as claimed in claim 1 and having the formula

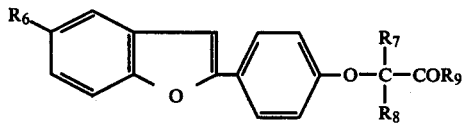

wherein $R_7$ is lower alkyl, $R_8$ is hydrogen or lower alkyl, $R_9$ is hydroxyl or lower alkoxy, and $R_6$ is hydrogen or halogen; or a pharmaceutically usable salt of said compounds with $R_9$ being hydroxyl.

8. A compound as claimed in claim 7 in which formula $R_7$ is n-pentyl or methyl, $R_8$ is hydrogen, $R_9$ is hydroxyl or ethoxy, and $R_6$ is hydrogen or fluorine; or a pharmaceutically usable salt of said compounds with $R_9$ being hydroxyl.

9. A compound as claimed in claim 7 in which formula each of $R_7$ and $R_8$ represent methyl, $R_9$ is hydroxyl or lower alkoxy, and R represents hydrogen; or a pharmaceutically usable salt of said compounds with $R_9$ being hydroxyl.

10. A compound as claimed in claim 1 and having the formula

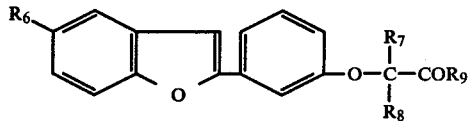

wherein $R_7$ is lower alkyl, $R_8$ is hydrogen or lower alkyl, $R_9$ is hydroxyl or lower alkoxy, and $R_6$ is hydrogen or halogen; or a pharmaceutically usable salt of said compounds with $R_9$ being hydroxyl.

11. A compound as claimed in claim 10 in which formula $R_7$ is n-pentyl or methyl, $R_8$ is hydrogen, $R_9$ is hydroxyl or ethoxy, and $R_6$ is hydrogen or fluorine; or a pharmaceutically usable salt of said compounds with $R_9$ being hydroxyl.

12. A compound as claimed in claim 10 in which formula each of $R_7$ and $R_8$ represent methyl, $R_9$ is hydroxyl or lower alkoxy, and $R_6$ represents hydrogen; or a pharmaceutically usable salt of said compounds with $R_9$ being hydroxyl.

* * * * *